United States Patent [19]
Papadakis et al.

[11] Patent Number: 5,461,921
[45] Date of Patent: Oct. 31, 1995

[54] DIRECT-SEQUENCE SPREAD-SPECTRUM ULTRASONIC TESTING DEVICE

[75] Inventors: Emmanuel P. Papadakis; Steve F. Russell; Samuel J. Wormley, all of Ames, Iowa

[73] Assignee: Iowa State University Research Foundation, Inc., Ames, Iowa

[21] Appl. No.: 91,179

[22] Filed: Jul. 13, 1993

[51] Int. Cl.[6] ............................................. G01N 29/10
[52] U.S. Cl. ............................ 73/628; 73/620; 73/602
[58] Field of Search .......................... 73/602, 628, 598, 73/600, 610, 620; 364/507, 508

[56] References Cited

U.S. PATENT DOCUMENTS

| | | | |
|---|---|---|---|
| 3,264,606 | 11/1964 | Crook et al. | 367/39 |
| 3,351,859 | 8/1964 | Groth, Jr. et al. | 375/1 |
| 3,390,391 | 11/1965 | Kissinger et al. | 342/201 |
| 3,756,071 | 9/1973 | Dory | 73/602 |
| 3,757,329 | 9/1973 | Sato et al. | 324/104 |
| 3,787,853 | 1/1974 | Brookner | 342/111 |
| 4,044,356 | 8/1977 | Fournier | 342/189 |
| 4,049,077 | 9/1977 | Mifsud | 367/39 |
| 4,053,889 | 10/1977 | Johnson | 342/201 |
| 4,167,879 | 9/1979 | Pedersen | 73/610 |
| 4,428,237 | 1/1984 | Zeger et al. | 73/592 |
| 4,443,799 | 4/1984 | Rubin | 342/210 |
| 4,463,608 | 8/1984 | Takeuchi et al. | 73/606 |
| 4,569,231 | 2/1986 | Carnes et al. | 73/626 |
| 4,598,293 | 7/1986 | Wong | 342/201 |
| 4,701,934 | 10/1987 | Jasper | 375/1 |
| 4,951,263 | 8/1990 | Shope | 367/2 |
| 4,977,786 | 12/1990 | Davis | 73/864.24 |
| 5,000,568 | 3/1991 | Trutna, Jr. et al. | 356/73.1 |
| 5,065,629 | 11/1991 | Koike et al. | 73/602 |
| 5,084,709 | 1/1992 | Baghdady | 342/442 |

OTHER PUBLICATIONS

"A Real–Time Correlation System For Ultrasonic Non–Destructive Testing"; F. K. Lam et al.; 28A International Journal of Electronics; vol. 53; No. 2; 1983; pp. 133–147.

Bilgutay, Nihat M., Burgason, Eric S. and Newhouse, Vernon L., "Evaluation of a Random Signal Correlation System for Ultrasonic Flaw Detection," *The Institute of Electrical and Electronics Engineers, Inc.*, Sep. 1976, pp. 229–333.

"Ultrasonic Correlation Testing of Highly Attenuating Materials," John Hopkins University Newsletter, CNDE, Summer 1991.

Primary Examiner—Hezron E. Williams
Assistant Examiner—Christine K. Oda
Attorney, Agent, or Firm—Flehr, Hohbach, Test, Albritton & Herbert

[57] ABSTRACT

Techniques for providing an ultrasonic flaw detection system are disclosed. A continuous wave of wide-band direct-sequence spread-spectrum signals continuously drives one or more transmitting transducers, thereby flooding a test object with coded ultrasound. In operation, the ultrasonic testing system is capable of reliably and predictably transmitting a high degree of ultrasonic energy (power) to a test object. Code division multiplexing correlation techniques using a variably delayed replica of a selected segment of the DSSS signal are applied to the signals received by the receiving transducers to generate a signature representing the signal returned from all reflectors within the test object.

58 Claims, 6 Drawing Sheets

DIRECT-SEQUENCE SPREAD-SPECTRUM ULTRASONIC TESTING DEVICE

FIELD OF THE INVENTION

The present invention relates to the field of nondestructive testing of materials, and more particularly to ultrasonic flaw detection systems.

BACKGROUND OF THE INVENTION

It is well recognized that the nation's infrastructure, particularly bridges, is subject to continuous deterioration from the elements. Accordingly, the preservation of the nation's infrastructure remains a growing concern. Bridges must be tested for growing and critical flaws because of the danger to the public of catastrophic failure. Ultrasonic flaw detection techniques can be used to detect and locate structural discontinuities, flaws or other differences or weaknesses in such structures. In addition, ultrasonic flaw detection techniques can be used in many other applications, including the interrogation of factory equipment, machinery, airplane wings, and the like.

With ultrasonic flaw detection techniques, a high-frequency mechanical vibrational energy (ultrasonic energy) is introduced into a test object to non-invasively and nondestructively probe the test object. Traditionally, the ultrasonic energy is transmitted to the test object by means of a transducer. Additionally, electromagnetic acoustic transducers (EMATs) could be employed which generate sound inside a conductive material. The transducer comprises an electromechanical device or piezoelectric material which converts the electric energy of a certain frequency into acoustic energy and also convert the acoustic energy back into electric energy of the same frequency.

First, an electrical signal is applied to the transducer which converts the received electric signal into ultrasonic energy. This ultrasonic energy is transmitted by mechanical bond or through a coupling liquid into a test object. The ultrasonic energy then transmits, reflects, and reverberates through the test object. A second ultrasonic transducer converts the ultrasound back into an electrical signal. Typically, the electrical signal is stored, displayed or otherwise processed to analyze the conditions which exist in the test object.

Currently, there are two primary methods employed for ultrasonic flaw detection. The most common method is classified as "pulse-echo." In pulse-echo systems, typically a single transducer is used for both transmitting and receiving the ultrasonic energy. The second method is classified as "through-transmission" or "pitch-catch." In through-transmission systems, separate transmitting and receiving transducers are employed.

In both of the above systems, short pulses of ultrasonic waves are launched as either plane waves or focused waves. To avoid overlapping the signals collected by the receiving transducer, the ultrasound is launched as short pulses of broad bandwidth that are separated far in time so that the reverberations of one pulse die out before the next pulse is transmitted. During the time span between the pulses, the receiving transducer continuously collects the transmitted, reflected, and reverberated ultrasonic energy of the initial short pulse.

The pulse-echo and through-transmission methods described above, while effective in some applications, have certain drawbacks and deficiencies. Importantly, the detectability of flaws is limited by the energy which can be transmitted per repetition time period of the above pulsing sequence. For example, to permit fine time resolution of the received signal, the pulses must be very short as compared to a relatively long repetition time period between pulses. The duration of a typical pulse may be of the order of 0.1 microsecond while a typical repetition time period between pulses may be of the order of 1000 to 10,000 microseconds. Thus, the duty cycle (pulse duration/repetitive time period) is $10^{-4}$ or $10^{-5}$.

Since the energy which can be used to detect flaws is proportional to the square of the voltage applied to the transducer times the duty cycle of the system, the capabilities of the above flaw detection techniques are limited by the dielectric strength (breakdown voltage) of the piezoelectric material. The breakdown voltage is fixed for a given dielectric material. Accordingly, the total energy useable to determine flaws within a structure is severely limited by the low duty cycle. Moreover, due to the limited energy capacity of the above systems, in order to interrogate a large area of a test object, scanning techniques must generally be used to scan the entire structure point-by-point. The scanning technique requires repeated interrogations at multiple positions along the structure to detect all flaws within the structure. Such techniques are typically, time-consuming, labor-intensive and often involve concomitant tear-down. In the case of bridges, the locations where pulse-echo transducers must be placed for adequate interrogation are often inaccessible.

To improve upon the low duty cycle restriction, one prior art method (described in U.S. Pat. No. 4,167,879 issued to Pedersen) transmits a narrow band pseudo-random coded and phase-modulated interrogation signal at a plurality of carrier frequencies toward the object to be tested. The interrogation signal has a plurality of discrete frequency, continuous wave carrier signals which are modulated by a relatively short repeating code signal. In operation, the respective carrier frequencies are discrete, and the carrier frequency is stepped. Different selected cells are sequentially interrogated by looking at different arrival times of the carrier. By cross-correlating the received signal with a delayed replica of the narrow band pseudo-random code, an improvement upon the low duty cycle restriction can be achieved.

The above method, however, also has certain drawbacks and deficiencies. Specifically, the above narrow band method results in interrogation signals which closely resemble sinusoidal waves. When the interrogation signals are demodulated (using frequency division multiplexing), the pseudo-random code is stripped and the information remaining is the difference between the amplitude and phase of the received signal and the original carrier. This difference provides only limited information about the flaws within the system. The above system also suffers from the constraints of requiring a relatively short code word to modulate the carrier signal. If the code word length is too great, the spectral lines in the output spectrum will be too close to each other to be adequately discriminated, and information regarding the flaws within the system will be lost.

SUMMARY OF THE INVENTION

Accordingly, a general object of the present invention is to provide a reliable and predictable ultrasonic flaw detection device capable of interrogating a large test object to determine all flaws within the test object and obviate the drawbacks and restrictions of previous methods.

Another object of the present invention is to provide an ultrasonic flaw detection device capable of transmitting a high degree of ultrasonic energy (power) into a test object without the restriction of a duty cycle.

Yet another object of the present invention is to provide an ultrasonic flaw detection device capable of transmitting a wide-band continuous wave of ultrasonic energy into a test object.

An additional object of the present invention is to provide an ultrasonic flaw detection device capable of interrogating a large volume of a test object, from single points of transmission and reception, to detect changes in volume, shape, dimension, composition, density, homogeneity, or acoustic velocity.

Another object of the present invention is to provide an ultrasonic flaw detection device which uses a wide-band direct-sequence spread-spectrum (DSSS) interrogation signal and a code division multiplexing technique for correlating the received signals.

The foregoing and other objects are, in the present invention, embodied in an improved apparatus for ultrasonic flaw detection. In accordance with one aspect of the present invention, flaw detection is achieved by using a wide-band spread-spectrum coded signal of a given carrier frequency to continuously drive one or more transmitting transducer, thereby flooding a test object with coded ultrasound. The transmitted ultrasonic energy transmits, reflects, and reverberates through the test object. To obtain the output, one or more receiving transducers receive the coded ultrasound, and a time-shifted cross-correlation technique is applied to a selected segment of the returned signal to generate a return signature signal representing all reflectors within the test object. Changes in the properties of the test object or flaws within the test object are determined by comparing the returned signature signal with a known-good signature signal or by applying expert knowledge techniques to the returned signature signal.

Thus, the present invention discloses an apparatus which can rapidly and efficiently determine all flaws within a test object. An advantage of the present invention includes the ability to provide an effective duty cycle of 1.0, with excellent time resolution, while the amplitude of each cycle of the ultrasonic signal source remains the maximum permissible for the dielectric strength of the piezoelectric element. This apparatus is different from prior devices which are traditionally limited by low duty cycle restrictions or the requirement of a narrow band interrogation signal and a carrier having a stepped and discrete frequency. The result is a gain of 50 to 60 dB in average energy (power) over pulse echo systems, and therefore, an equivalent increase in the detectability of flaws. The increased energy (power) may be utilized 1) to find flaws further inside materials or further away from the transmitting transducer, 2) to find smaller flaws, 3) to find flaws in a shorter time, or 4) to find flaws in a much larger volume.

While the invention will be described in connection with certain preferred embodiments, it is not intended that the invention be limited to those specific embodiments but rather that it be accorded a broad scope commensurate with the appended claims, consistent with the prior art.

BRIEF DESCRIPTION OF THE DRAWINGS

FIG. 3a represents the received signal for a test object having no flaws and FIG. 3b represents the received signal for the same test object after the introduction of a flaw.

DETAILED DESCRIPTION OF CERTAIN PREFERRED EMBODIMENTS

Figure 1:
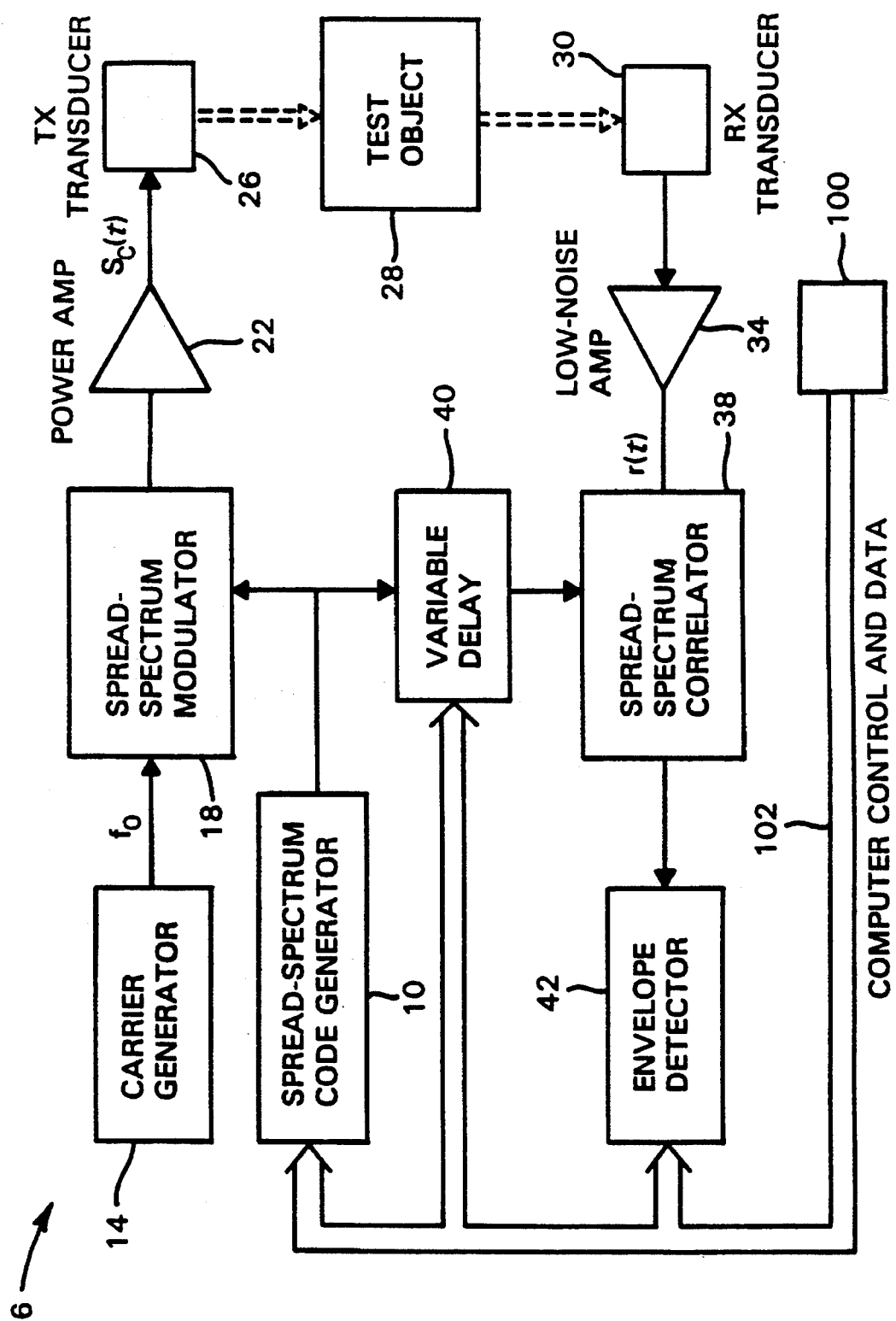
FIG. 1 is a block diagram of a preferred embodiment of the present invention, in the form of a single-channel ultrasonic flaw detection system, showing the arrangement of some of its major elements.

Referring to FIG. 1, there is shown a block diagram of a preferred embodiment of the present invention in the form of a single-channel ultrasonic flaw detection system 6. In operation, a test object 28 is flooded with continuous waves of coded ultrasound by a transmitting transducer 26. The ultrasound transmits, reflects, and reverberates through the test object 28 and is then collected by a receiving transducer 30. As a result, the ultrasonic flaw detection system 6 must be able to distinguish between each of the ultrasonic waves within the test object 28 as they are received by the receiving transducer 30.

Accordingly, the ultrasonic flaw detection system 6 includes a spread-spectrum code generator 10. The code generator 10 creates a binary pulse-amplitude-modulation (BPAM) signal with a pseudo-random code sequence. The pseudo-random code sequence used is long enough so that the propagation time for all acoustic returns is exceeded before the code repeats. By using a non-repeating segment of a long pseudo-random code sequence, independent signals having the same pseudo-random code can not overlap in time, and thus, false correlation is eliminated. However, the random code sequence is also short enough so that the time necessary to correlate the output is not excessive. A long code length also contributes to generate a signal having spectral components which are in substantial continuum. An example of a range of bit lengths is from $2^{16}$ to $2^{48}$.

The ultrasonic flaw detection system 6 also includes a carrier generator 14. The carrier generator 14 is adjustable to change the frequency of the carrier output depending upon the object to be tested. For large structures, such as bridges, typically a carrier having a lower frequency is more desirable whereas for smaller structures, such as a ball bearing, a carrier having a higher frequency is preferable. However, during a given interrogation, the carrier generator 14 produces a sinusoidal carrier signal with a constant carrier frequency, fo, which need not be changed in order to derive the necessary information from an interrogation.

As can be seen in FIG. 1, a spread-spectrum modulator 18 then phase-modulates the carrier signal using the BPAM signal to produce a wide-band Direct-Sequence Spread-Spectrum (DSSS) signal which, after linear amplification, is denoted as $S_c(t)$. The spread-spectrum code generator 10 ensures that the BPAM signal has a high enough chipping rate to ensure a wide spreading bandwidth for the DSSS signal at the output of the spread-spectrum modulator 18. By varying the chipping rate, the bandpass of the transducer is filled to maximize the signal energy coupled through the system. Moreover, the modulator phase-modulates the carrier with the pseudo-random coded signal to generate the continuous wave wide-band DSSS signal, where the coded signal has a code length which is sufficiently high to produce spectral components in the DSSS signal which are in substantial continuum. An example of a range of bit lengths is from $2^{16}$ to $2^{48}$. Since the DSSS signal is a wide-band signal which is derived from a long code sequence, the fourier transform of the wide-band DSSS signal appears quite noisy without any distinguishable discrete spectral components.

In a preferred embodiment of the present invention, the governing equation is:

$$S_c(t) = A_c \cos [2\pi f_o t + d(t, T_c)*(\pi/2) + \Phi_o]$$

where $A_c$ is the signal amplitude, $f_o$ is the carrier frequency, $d(t,T_c)$ is the binary pseudo-random noise modulation signal (spreading code), $T_c$ is the width of one chip, and $\Phi$ is an arbitrary carrier phase. The pulse amplitudes of the BPAM spreading code $d(t,T_c)$ are pseudo-randomly chosen to be either +1 or −1. The amplitude spectral density function for the wide-band DSSS is a sinc function, and the spectral bandwidth-between-first-nulls is $2/T_c$.

In the embodiment shown in FIG. 1, an input amplifier 22 receives the wide-band DSSS signal from the bi-phase modulator 18 and drives the transmitting transducer 26, which may operate up to its continuous wave (CW) power limit. The transmitting transducer 26 converts the wide-band DSSS signal into ultrasonic energy and transmits the coded ultrasound into the test object 28 either directly or through a coupling medium. As a result, the test object 28 is flooded with the coded ultrasound.

Figure 2:
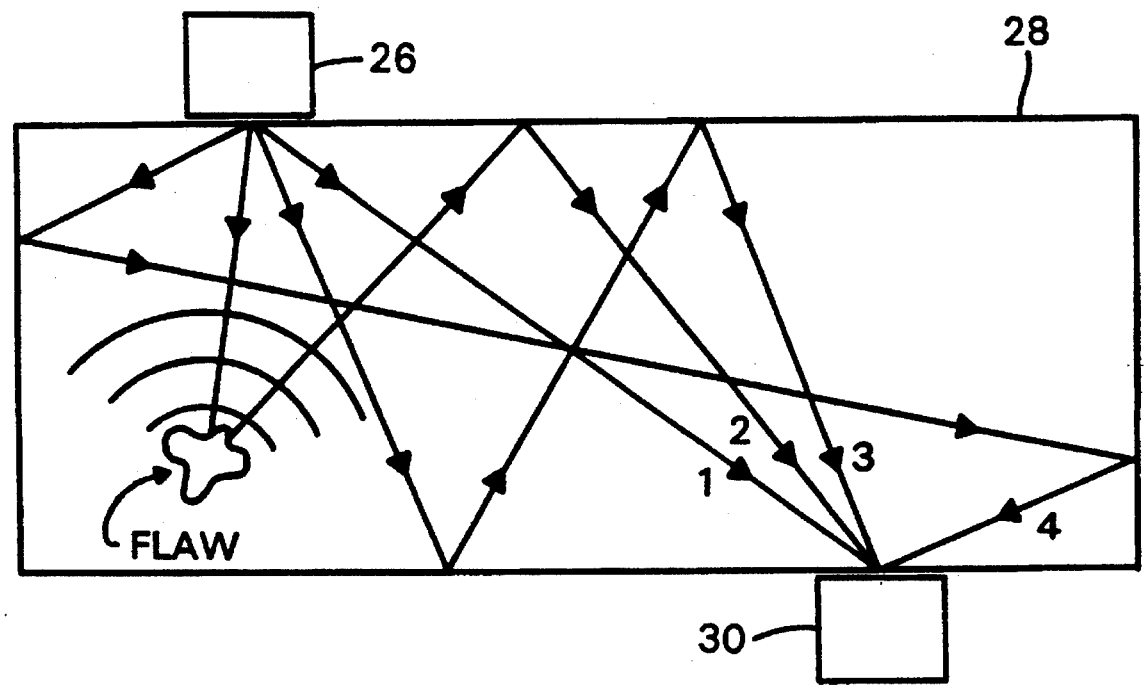
FIG. 2, is a pictorial representation of typical paths that the coded ultrasound travels through a test object as a result of the diffraction and reflection of the ultrasonic signal.

To increase the area of coverage within the test object 28, beam spreading of the coded ultrasound is employed. Beam spreading occurs as a result of the design of the transmitting transducer 26. The transmitting transducer 26 is shaped so that the ultrasonic waves are incident on the test object 28 at a plurality of angles. Referring to FIG. 2, there is shown a pictorial representation of typical traveling paths that the coded ultrasound takes as a result of the diffraction and reflection of the ultrasound. As shown in FIG. 2, the coded ultrasound transmits, reflects, and reverberates through the test object 28 and is then collected by the receiving transducer 30.

In the embodiment shown in FIG. 1, a low noise output pre-amplifier 34 is employed to receive and amplify the electric signal generated by the receiving transducer 30. Then, a spread-spectrum correlator 38 is used to correlate the received signal, r(t), by stripping the spread-spectrum code. Variable delay circuitry 40 provides the spread-spectrum correlator 38 with a delayed replica of the original spread-spectrum code for use in code stripping (i.e. despreading). The output of the spread-spectrum correlator 38 produces a sinusoidal signal (modified carrier signal) of the same frequency, $f_o$, as the original carrier but with a different amplitude and phase (modified due to traversing acoustically through the test object). The amplitude (or equivalent envelope power) of this sinusoidal signal is the cross-correlation function shown in FIG. 3b and is a function of the variable delay of the pseudo-random spreading code. An envelope detector 42 is used to measure the amplitude values (or equivalent envelope power) of the sinusoidal signal produced by the spread-spectrum correlator 38 as a function of the variable delay. Alternatively, a costas demodulator may be employed to synchronously determine the envelope power. In a preferred embodiment a narrow band filter is used to average small amplitude variations of the modified carrier signal. Alternatively, a running integrator could be employed to filter or smooth the amplitudes. The range of envelope power to variable delay provides the information regarding flaws or other changes in the various properties of the test object such as volume, shape, dimension, composition, density, homogeneity, or acoustic velocity.

Figure 3A:
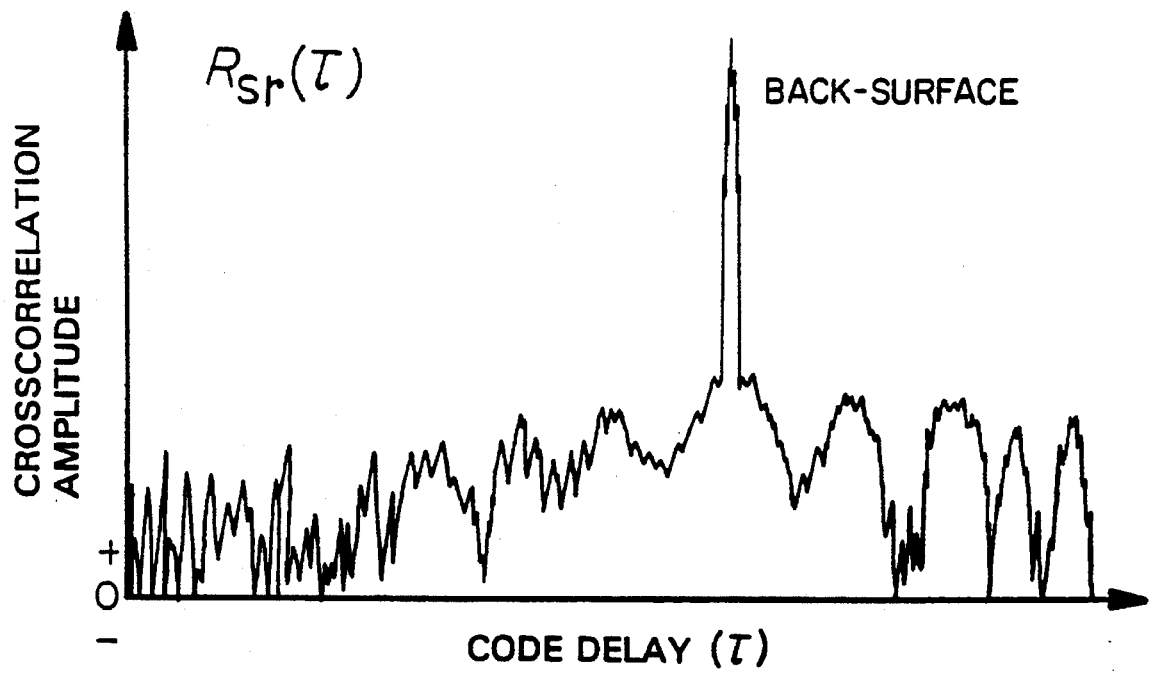
FIG. 3a and FIG. 3b are plots of typical correlator output signals which may be acquired using the embodiments shown in FIG. 1 and/or FIG. 5.
Figure 3B:
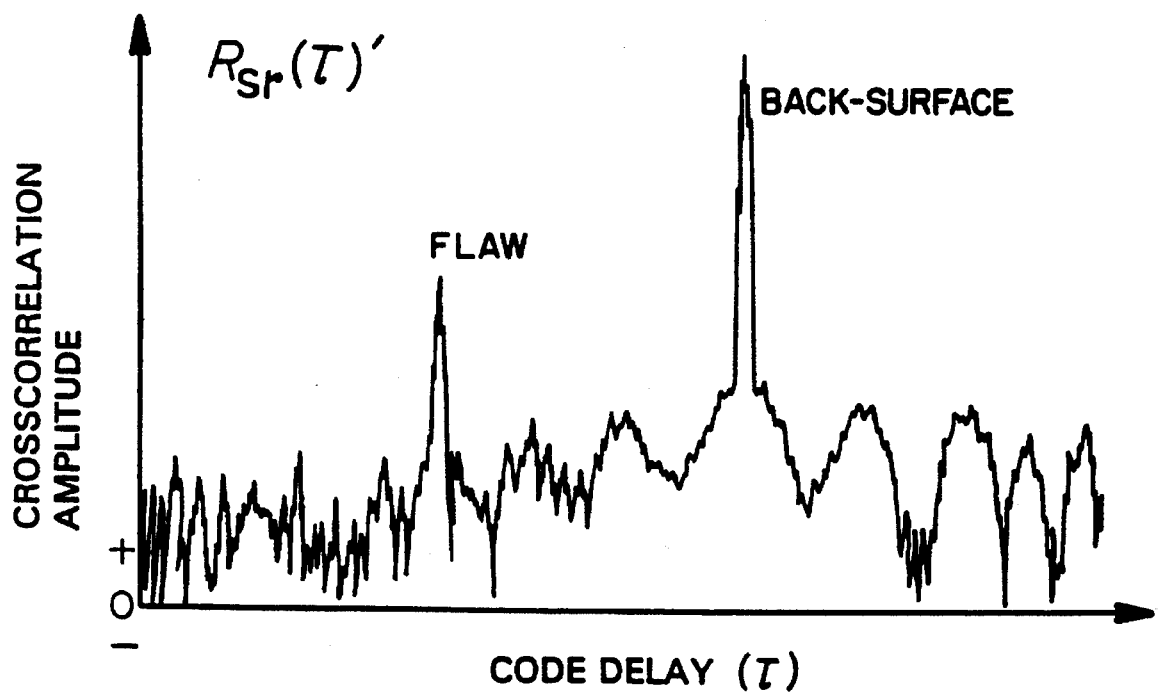

Referring to FIG. 3a, there is shown a graphical representation of a typical cross-correlation function output produced by the ultrasonic flaw detection system of the present invention. The output of the ultrasonic flaw detection system 6 is the amplitude of the cross-correlation function as determined by the envelope detector 42 as a function of variable delay of the pseudo-random code. The data in FIG. 3a represents a unique signature signal obtained by the ultrasonic flaw detection system 6 when the test object 28 was known to contain no flaws, i.e. when the properties of the test object such as volume, shape, dimension, composition, density, homogeneity, or acoustic velocity are all within acceptable tolerances. This first signature is stored in the memory 106, and may also be backed-up and stored on the hard disk 107 for later retrieval. FIG. 3b. shows a second signature signal obtained from the same test object 28 by the ultrasonic flaw detection system 6 at a later date. This second signature is stored in the memory 106. The difference between the data shown in FIG. 3a and the data shown in FIG. 3b identifies a change ("flaw") in one of the properties of the test object 28. This difference is obtained, for example, by subtracting the stored second signature from the stored first signature. The subtraction is performed by the controller 104, and the results are stored in the memory 106 and displayed on the display 108. The resulting difference is shown in FIG. 3c.

Figure 3C:
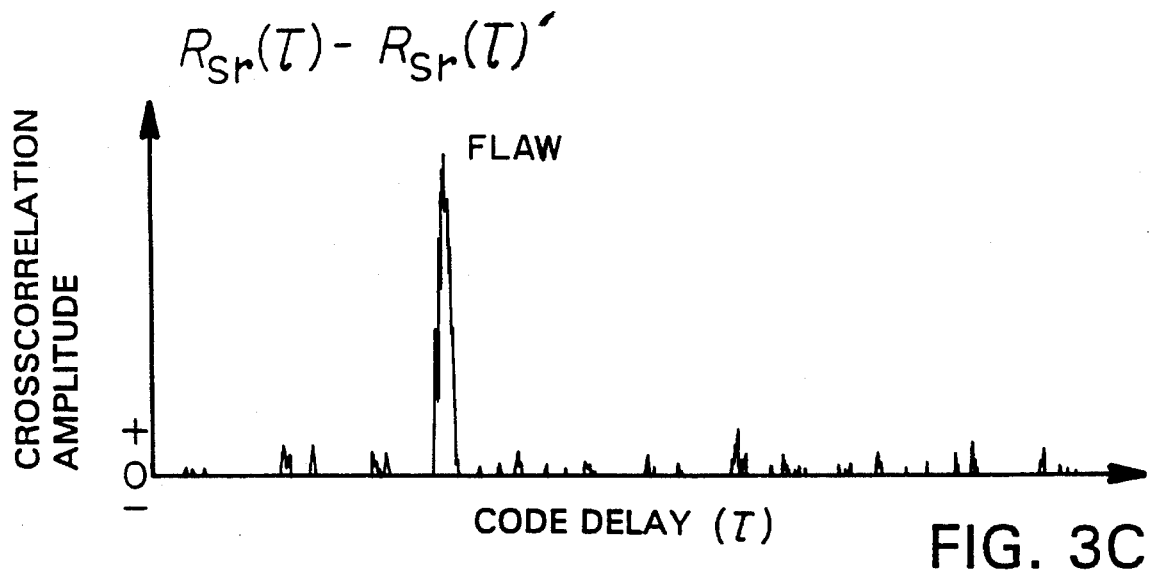
FIG. 3c shows the signal resulting from the subtraction of the signals shown in FIG. 3a and FIG. 3b.

As can be seen in FIGS. 3a through 3c, the variable delay is changed in discrete steps as opposed to a continuous range, causing jagged edges and sharp peaks in the displayed output. This granularity in the display has no effect on the quality of the information but is merely an artifact of displaying numerical information using graphical means. The ultrasonic flaw detection system 6 is adaptive so that the discrete steps in the variable delay can be chosen to provide the optimum delay for a given test object. Accordingly, the range of variable delay is predetermined depending upon, among other things, 1) the size of the test object 28, 2) the amount of attenuation in the test object 28, and 3) the desired scope of the inspection. In this context, the scope of the inspection refers primarily to the location of expected flaws in the test object. Flaws located far from the transducer require longer sequences to avoid echo ambiguity. If the flaw is small relative to the test object, wider spreading bandwidth and longer sequences are required.

As mentioned above, the pseudo-random code sequence used is long enough so that the propagation time for all significant acoustic returns is exceeded before the code repeats. As a result, sometimes it is not possible or even desirable for the spread-spectrum correlator to correlate the received signal over the entire range of the code word. Accordingly, a technique called partial-length correlation is employed to correlate the received signal over a segment of the code word length. This segment represents a time delayed partial-length code replica of the originally transmitted code. For example, with partial-length correlation, a code word having 10 million bits may be correlated over a word segment beginning with bit 1,000,000 through bit 6,000,000.

With this partial-length correlation technique, the envelope detector 42 has a variance in the estimate of the cross-correlation function. The variance of the estimate will increase as the length of the partial correlation decreases. Accordingly, the probability of detection goes down if a relatively small segment of the code word is used to correlate the received signal. The specific length of the code word is determined on an application by application basis. If processing time is at a premium, and a small decrease in the probability of detection is not a primary concern, a relatively short partial-length code segment can be chosen. Conversely, if the optimum in probability of detection is the primary objective, this can be achieved—at the cost of increasing the processing time—by choosing a larger partial-length code segment. In some applications, it may be desirable to choose a segment equal to the entire length of the code and correlate over the full code length.

Figure 4:
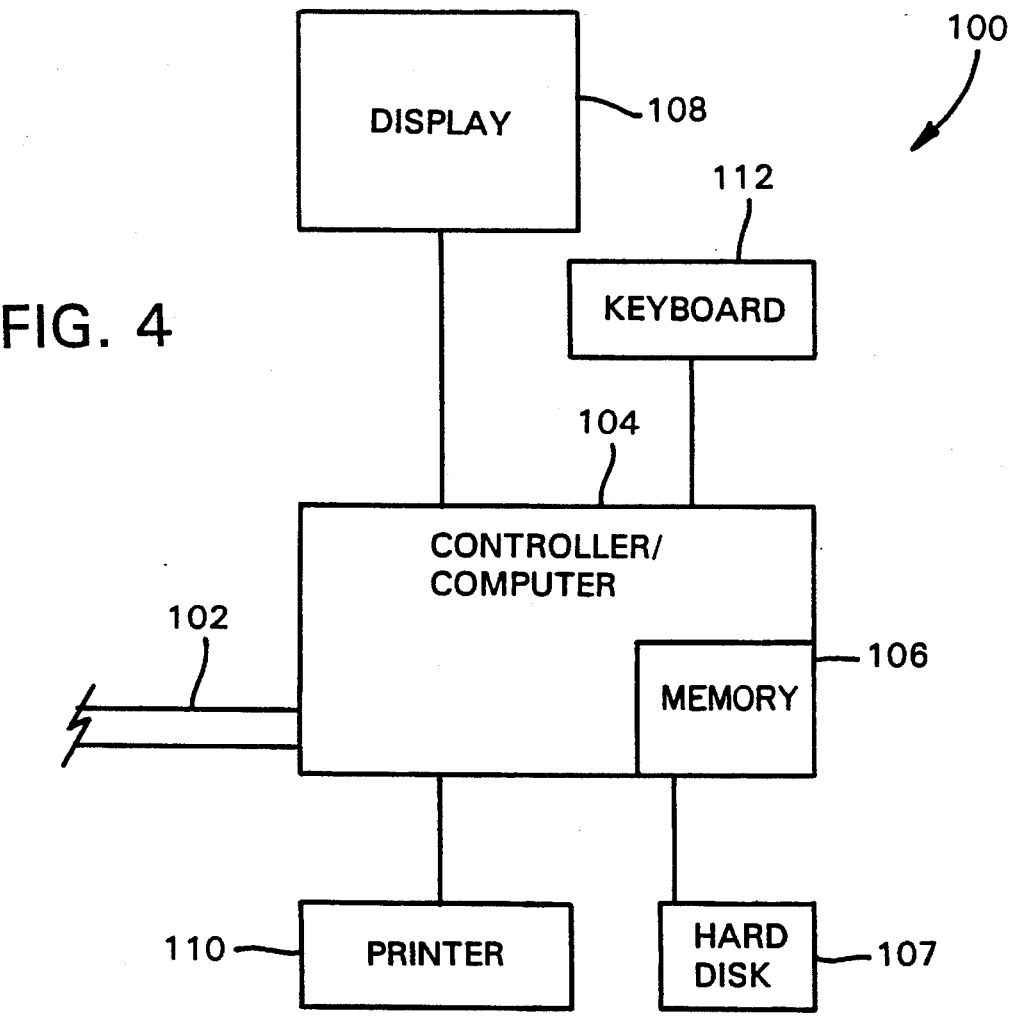
FIG. 4 shows a control system and a signal processing computer which may be used to control, process, and display information for the embodiments shown in FIG. 1, FIG. 5 and FIG. 6.

In a preferred embodiment of the present invention, there is provided a control system which controls the operation of the ultrasonic flaw detection system 6. Referring to FIG. 4, there is shown a control and processing system 100, suitable for controlling and processing the embodiments shown in FIG. 1, FIG. 5 and FIG. 6, consisting generally of a controller/computer 104, a display 108, a printer 110, and a keyboard 112. The controller/computer 104 may be any of several computer boards available for general computation and peripheral device control. It may be of the type referred to as a 486-66 motherboard; however, other microprocessor-based controller/computers may be substituted without deviating from the present invention. In another preferred embodiment of the present invention, a parallel processor architecture is used to speed the processing of the time-consuming calculations. The display 108 and the keyboard 112 are compatible with the 486-66 motherboard but variations and substitutions, known to those skilled in the art, may also be employed.

Software for the controller/computer 104 may, for example, be written in the C or FORTRAN programming languages. However, other computer languages may be substituted by those skilled in the art, if desired. The software allows the controller/computer 104 to, among other things, control the carrier generator 14, the envelope detector 42, the variable delay circuitry 40 and the spread-spectrum code generator 10, as well as the timing and synchronization between the above components. The controller/computer 104 also receives the output of the envelope detector 42 and can display the signature signal of the test object 28 on the screen of the display 108 or by printing the signature signal on the attached printer 110. The controller/computer 104 also analyzes the test object signature signal obtained and compares it with signature signals previously obtained to determine if changes in the acoustic properties of the test object have occurred.

Typically, the invention operates and is used as follows. First, the operator uses the keyboard 112 to select the various parameters which control the ultrasonic flaw detection system 6. The parameters which the operator can choose in the illustrated embodiment of the present invention include: 1) the carrier frequency, 2) the code chipping rate, 3) the code word length, 4) the length of the code word segment used for partial correlation, 5) the range of delay time from the reference code epoch, 6) test object identification and parameters, 7) artificial intelligence parameters, 8) detection thresholds and statistical confidence intervals, and 9) recording and display options. Of course, it is appreciated that both the selection and the range of possible parameters depend upon the specific application and the desired results.

After the test is completed, the controller/computer 104 stores the signature signal of the test object in the memory 106 of the controller/computer 104 and compares the recently stored signature signal with a previously stored signature signal (stored on a hard disk 107) of the test object 28 to determine whether any flaws (or other irregularities) have formed within the test object 28. Changes in the properties of the test object 28 or the flaws within the test object 28 can also be separated from the background by applying expert knowledge. The memory 106 is also used to store the operating routines which drive the controller/computer 104 as herein described, including a standard operator interface routine, data acquisition routine, data processing routine, data display routine, instrumentation control routine, and data analysis routine. Other preferred embodiments of the present invention use artificial intelligence (AI) techniques to interpret flaw signals. By using AI techniques, other preferred embodiments of the present invention function independently of an operator and operate at scheduled intervals to continuously search for flaws within a test object.

Referring again to FIG. 1, the receiving transducer 30 is attached to the test object 28 at a single point, either physically or through a coupling medium. By attaching the receiving transducer 30 at different locations around the test object 28, or by attaching more than one receiving transducer to the test object 28, signals returned from a variety of observation points can be combined to provide more detailed information about the test object 28. Similarly, multiple transmitting transducers 26, and multiple receiving transducers 30, can also be employed.

Figure 5:
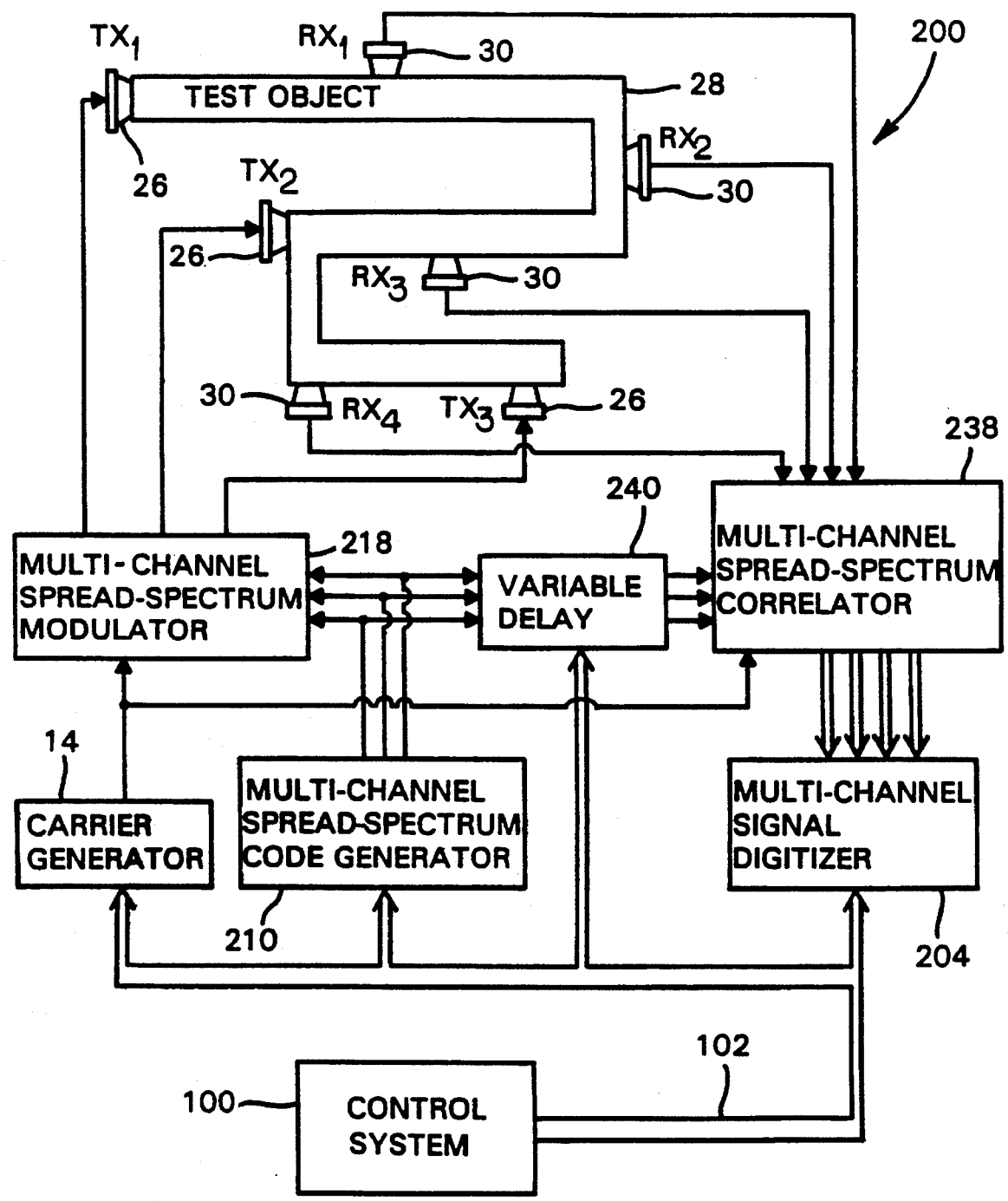
FIG. 5 is a schematic diagram of another preferred embodiment of the present invention, in the form of a multi-channel, multi-sensor ultrasonic flaw detection system, showing the arrangement of some of its major elements.

Referring to FIG. 5, there is shown another preferred embodiment of the present invention in the form of a multi-code, multi-sensor ultrasonic flaw detection system 200. Identically referenced numerals in FIG. 5 correspond to identically referenced components of FIG. 1 and function similarly. As a result, the operation of the embodiment shown in FIG. 5 is very similar to the operation of the embodiment shown in FIG. 1, except that a plurality of transmitting transducers 26 and receiving transducers 30, are employed. By positioning multiple transmitting and receiving transducers at predetermined locations around the test object 28, code-division multiplexing is used to increase the ultrasound "flooding" effect and also increase the information regarding the changes that have occurred in the test object since it was last inspected. This embodiment also provides for the gathering of information regarding the test object in a shorter time period.

In the embodiment shown in FIG. 5, a multi-channel spread-spectrum modulator 218 receives a carrier signal from the carrier generator 14 and splits the carrier signal into three identical carrier signals. The three carrier signals are then phase modulated using three separate BPAM signals generated by the multi-channel spread-spectrum code generator 210. The resulting wide-band DSSS signals (after amplification—not shown) are applied to the transmitting transducers 26. The transmitting transducers 26 flood the test object 28 with coded ultrasound, and the received signals are collected by the receiving transducers 30. A multi-channel spread-spectrum correlator 238 is employed to independently correlate each of the received signal using the original carrier signal and delayed replicas of the original spread-spectrum codes. The output of the spread-spectrum multi-channel correlator 238 is then digitized by a multi-channel signal digitizer 204 and sent to the control system 100 for processing as described above.

Figure 6:
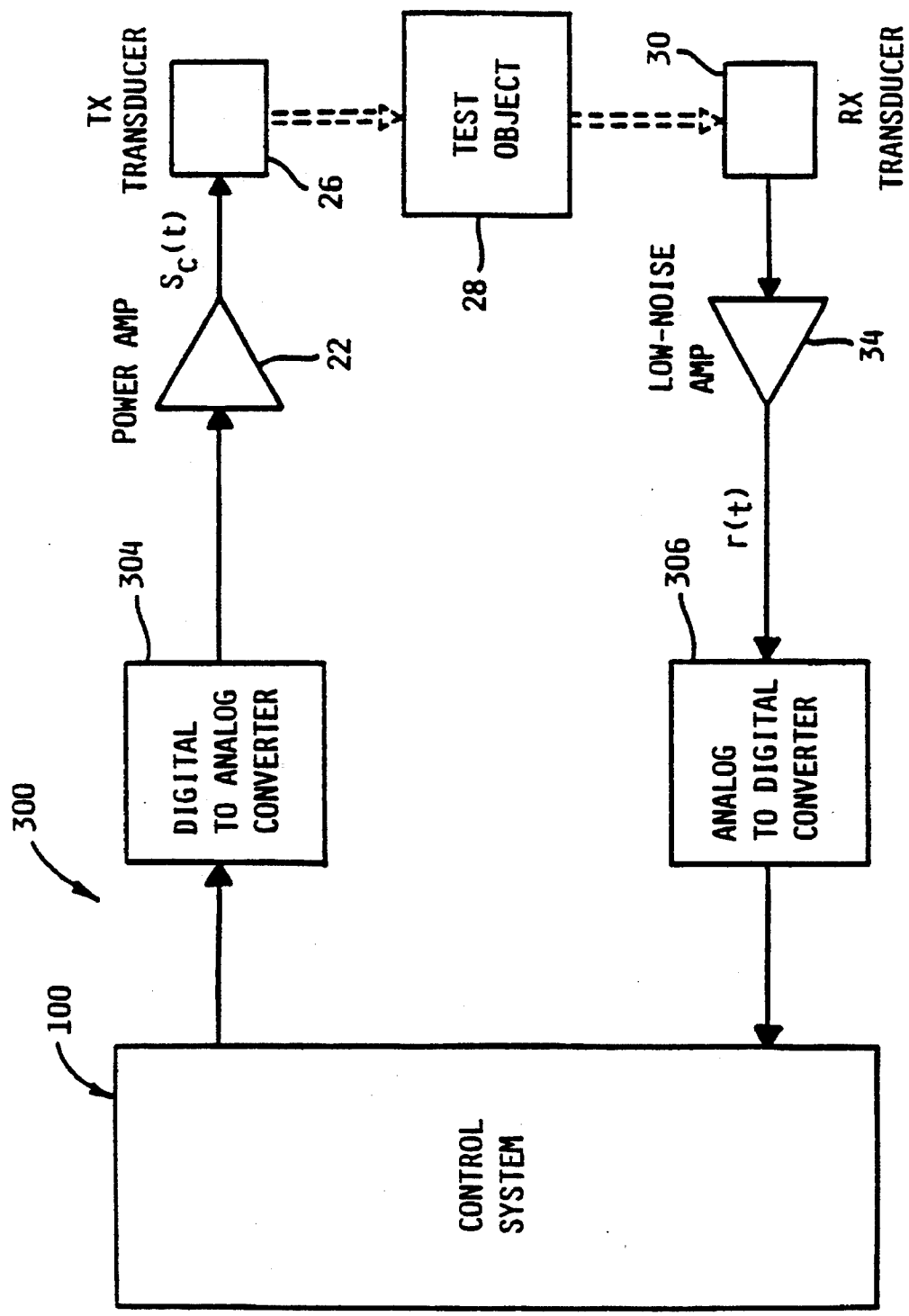
FIG. 6 is a schematic diagram of another preferred embodiment of the present invention, in the form of an ultrasonic flaw detection system, wherein the signal processing functions are primarily performed in software.

It should be readily appreciated by those skilled in the art that the signal processing functions described in the above embodiments may be implemented using a variety of combinations of hardware and software devices other than those described above. For example, there is shown in FIG. 6 another preferred embodiment of the present invention, in the form of an ultrasonic flaw detection system 300, wherein the signal processing functions are primarily performed in software by the controller/computer 104 of the control system 100. Identically referenced numerals in FIG. 6 correspond to identically referenced components of FIG. 1 and function similarly. As a result, the operation of the embodiment shown in FIG. 6 is again very similar to the operation of the embodiment shown in FIG. 1. In addition, the ultrasonic flaw detection system 300 of FIG. 6 may also be adapted to the embodiment shown in FIG. 5 having a plurality of transmitting and receiving transducers.

In the embodiment shown in FIG. 6, the control system 100 generates a digital wide-band Direct-Sequence Spread-Spectrum (DSSS) signal representing a carrier signal that has been phase-modulated by a pseudo-random code sequence. The digital wide-band DSSS signal is applied to a digital-to-analog converter 304 which converts the digital wide-band DSSS signal to an analog wide-band DSSS signal. After linear amplification by the power amplifier 22, the analog wide-band DSSS signal is denoted as $S_c(t)$. As described above, the transmitting transducer 26 converts the wide-band DSSS signal into ultrasonic energy and transmits the coded ultrasound into the test object 28. After transmitting, reflecting, and reverberating through the test object 28, the coded ultrasound is collected by the receiving transducer 30 and amplified by the low noise output pre-amplifier 34. An analog-to-digital converter 306 then converts the received ultrasonic signals to digital signals and provides the digital signals to the control system 100 for processing.

The control system 100 in FIG. 6 performs the signal processing provided by the variable delay 40 and the spread-spectrum correlator 38 of FIG. 1—namely, the control system 100 employs the code division multiplexing technique described above to correlating the received signals. By generating the delay code and correlating the received ultrasonic signals in software, greater system flexibility is achieved. The correlated digital signal can then be further processed by the control system 100 as described above. In a preferred embodiment, a LeCroy Model-9100 Function Generator may be used as the analog-to-digital converter 304, and the analog-to-digital converter 306 may be a LeCroy Model-9310L Digital Oscilloscope and Data Acquisition Unit. The converters 304 and 306 may be directly connected to the IEEE-488 interface of the controller/computer 104 of the control system 100.

What is claimed is:

1. An ultrasonic testing device comprising:

means for phase-modulating a carrier signal with a pseudo-random coded signal to generate a continuous wave wide-band electrical input signal, the coded signal having a code length which is sufficiently high to produce spectral components in the electrical input signal which are in substantial continuum;

transmitting means responsive to the electrical input signal and acoustically coupled to a test object for transmitting an ultrasonic interrogation signal having the spectral components of the electrical input signal into the test object;

receiving means acoustically coupled to the test object for receiving an ultrasonic signal returned from the test object in response to the ultrasonic interrogation signal and for converting the received signal into an electrical output signal; and means for cross-correlating the electrical output signal with a segment of a time-delayed replica of the pseudo-random coded signal to demodulate the electrical output signal and obtain a signal response from the test object.

2. The ultrasonic testing device of claim 1 further comprising means responsive to said cross-correlating means for producing a unique signature signal comprising the response of the test object to the ultrasonic interrogation signals as a function of variable time-delay.

3. The ultrasonic testing device of claim 2 wherein the means responsive to the cross-correlating means comprises an envelope detector which measures the envelope power of the demodulated output signal.

4. The ultrasonic testing device of claim 2 wherein the means responsive to the cross-correlating means comprises a costas demodulator to synchronously determine the power of the demodulated output signal.

5. The ultrasonic testing device of claim 2 wherein the variable time-delay range is predetermined based upon the desired scope of the inspection, wherein the scope of the inspection is defined as one of geometrical location and resolution.

6. The ultrasonic testing device of claim 2 further comprising means for displaying said unique signature signal.

7. The ultrasonic testing device of claim 2 further comprising means for analyzing said unique signature signal to determine the properties of the test object.

8. The ultrasonic testing device of claim 7 wherein said means for analyzing includes a controller which compares said unique signature signal with a previously stored signature signal.

9. The ultrasonic testing device of claim 1 wherein the phase-modulating means comprises:

a carrier generator for providing the carrier signal;

a spread-spectrum code generator providing the pseudo-random coded signal; and a direct-sequence spread-spectrum modulator for combining the carrier signal and the pseudo-random coded signal to produce the continuous wave wide-band electrical input signal.

10. The ultrasonic testing device of claim 1 wherein the pseudo-random coded signal ranges between $2^{16}$ and $2^{48}$ bits long.

11. The ultrasonic testing device of claim 1 wherein the segment comprises a partial-length segment.

12. The ultrasonic testing device of claim 11 wherein the probability of detection is increased by increasing the length of the partial-length segment.

13. The ultrasonic testing device of claim 11 wherein the required processing time is decreased by decreasing the length of the partial-length segment.

14. The ultrasonic testing device of claim 1 wherein a phase-modulating chipping rate is varied to maximize signal energy coupled through the transmitting and receiving means.

15. The ultrasonic testing device of claim 1 wherein a non-repeating segment of the pseudo-random code sequence is used to eliminate false correlation.

16. An ultrasonic testing device for interrogating a test object to determine the flaws within the test object comprising:
- a modulator for phase-modulating a carrier signal with a pseudo-random coded signal to provide a continuous wave wide-band electrical input signal;
- a transmitting transducer responsive to said electrical input signal, wherein said transmitting transducer transmits a coded ultrasonic interrogation signal into the test object;
- a receiving transducer responsive to an ultrasonic signal returning from the test object, wherein said receiving transducer provides an electrical output signal; and
- a correlator for cross-correlating the electrical output signal using a segment of a time-delayed replica of the pseudo-random coded signal to obtain a signal response from the test object.

17. The ultrasonic flaw detection device of claim 16 further comprising a detector for determining a unique signature signal comprising the response of the test object to the ultrasonic interrogation signals as a function of variable time-delay.

18. The ultrasonic flaw detection device of claim 17 wherein the detector comprises an envelope detector which measures the a demodulated output signal envelope power.

19. The ultrasonic flaw detection device of claim 17 wherein the detector comprises a costas demodulator to synchronously determine a demodulated output signal power.

20. The ultrasonic flaw detection device of claim 17 wherein the variable time-delay range is predetermined based upon the desired scope of the inspection, wherein the scope of the inspection is defined as one of geometrical location and resolution.

21. The ultrasonic flaw detection device of claim 17 further comprising a controller electrically connected to said detector.

22. The ultrasonic flaw detection device of claim 21 wherein the controller is configured to provide for the selection of operator selected control parameters which govern the manner in which the ultrasonic flaw detection device operates during an interrogation, said operator selected control parameters including the carrier frequency, the code chipping rate, the code word length, and the time delay of the time-delayed replica.

23. The ultrasonic flaw detection device of claim 21 wherein the controller is configured to compare said unique signature signal with a previously stored signature signal to determine the properties of the test object.

24. The ultrasonic flaw detection device of claim 16 wherein the transmitting transducer provides for beam spreading of the ultrasonic interrogation signal.

25. The ultrasonic flaw detection device of claim 16 wherein the pseudo-random coded signal ranges between $2^{16}$ and $2^{48}$ bits long.

26. The ultrasonic flaw detection device of claim 16 further comprising a plurality of transmitting transducers.

27. The ultrasonic flaw detection device of claim 16 further comprising a plurality of receiving transducers.

28. The ultrasonic flaw detection device of claim 16 further comprising a plurality of transmitting transducers and a plurality of receiving transducers.

29. The ultrasonic flaw detection device of claim 16 wherein the segment comprises a partial-length segment.

30. The ultrasonic flaw detection device of claim 29 wherein the probability of detection is increased by increasing the length of the partial-length segment.

31. The ultrasonic flaw detection device of claim 29 wherein the required processing time is decreased by decreasing the length of the partial-length segment.

32. The ultrasonic flaw detection device of claim 16 wherein the pseudo-random code has a code length which is sufficiently high to produce spectral components in the electrical input signal which are in a substantial continuum.

33. The ultrasonic flaw detection device of claim 16 wherein a phase-modulating chipping rate is varied to maximize signal energy coupled through the transmitting and receiving transducers.

34. The ultrasonic flaw detection device of claim 16 wherein a non-repeating segment of the pseudo-random coded signal is used to eliminate false correlation.

35. A method for interrogating a test object comprising the steps of:
- providing a carrier signal;
- phase-modulating the carrier signal with a pseudo-random coded signal to generate a continuous wave of wide-band electrical input signals;
- converting the electrical input signals into ultrasonic interrogation signals and transmitting the ultrasonic interrogation signals into the test object;
- receiving the ultrasonic interrogation signals from the test object and converting the received interrogation signals into electrical output signals;
- providing a time-delayed replica of the pseudo-random coded signal; and
- cross-correlating the electrical output signals using a segment of the time-delayed replica of the pseudo-random coded signal to obtain a signal response from the test object.

36. The method of claim 35 further comprising the step of measuring the amplitude of the cross-correlated signal as a function of variable time-delay to obtain a unique signature signal for the test object.

37. The method of claim 36 wherein the variable time-delay range is predetermined based on the desired scope of the inspection, wherein the scope of the inspection is defined as one of geometrical location and resolution.

38. The method of claim 36 further comprising the step of analyzing the signature signal obtained from the test object to determine the properties of the test object.

39. The method of claim 36 wherein the signature signal is compared with a signature signal previously obtained for the test object.

40. The method of claim 35 wherein the pseudo-random code has a code length which is sufficiently high to produce spectral components in the electrical input signal which are in a substantial continuum.

41. The method of claim 35 wherein a phase-modulating chipping rate is varied to maximize signal energy coupled through the transmitting and receiving steps.

42. The method of claim 35 wherein a non-repeating segment of the pseudo-random code sequence is used to eliminate false correlation.

43. The method of claim 35 wherein the segment comprises a partial-length segment.

44. The method of claim 43 wherein the probability of detection is increased by increasing the length of the partial-length segment.

45. The method of claim 43 wherein the required processing time is decreased by decreasing the length of the partial-length segment.

46. An ultrasonic testing device comprising:

means for providing a wide-band direct-sequence spread-spectrum (DSSS) interrogation signal representing a carrier signal phase-modulated with a pseudo-random coded signal and having spectral components which are in substantial continuum;

a transmitting transducer responsive to said DSSS interrogation signal wherein said transmitting transducer transmits a coded ultrasonic interrogation signal into the test object;

a receiving transducer responsive to an ultrasonic signal returning from the test object, wherein said receiving transducer provides an electrical output signal; and means for cross-correlating said electrical output signal using a segment of a time-delayed replica of the pseudo-random coded signal to obtain a signal response from the test object.

47. The ultrasonic testing device of claim 46 further comprising means responsive to the cross-correlating means for producing a unique signature signal comprising the response of the test object to the ultrasonic interrogation signals as a function of variable time-delay.

48. The ultrasonic testing device of claim 47 wherein the cross-correlating means and means responsive to the cross-correlating means include a software-driven controller.

49. The ultrasonic testing device of claim 47 wherein the variable time-delay range is predetermined based upon the desired scope of the inspection, wherein the scope of the inspection is defined as one of geometrical location and resolution.

50. The ultrasonic testing device of claim 47 further comprising means for displaying said unique signature signal.

51. The ultrasonic testing device of claim 47 further comprising means for analyzing said unique signature signal to determine the properties of the test object.

52. The ultrasonic testing device of claim 51 wherein said means for analyzing includes a controller which compares said unique signature signal with a previously stored signature signal.

53. The ultrasonic testing device of claim 46 wherein the means for providing a wide-band DSSS signal includes a software-driven controller.

54. The ultrasonic testing device of claim 46 wherein the pseudo-random coded signal ranges between $2^{16}$ and $2^{48}$ bits long.

55. The ultrasonic testing device of claim 46 wherein the segment comprises a partial-length segment.

56. The ultrasonic testing device of claim 55 wherein the probability of detection is increased by increasing the length of the partial-length segment.

57. The ultrasonic testing device of claim 55 wherein the required processing time is decreased by decreasing the length of the partial-length segment.

58. The ultrasonic testing device of claim 46 wherein a non-repeating segment of the pseudo-random code sequence is used to eliminate false correlation.

* * * * *